United States Patent
Rigla et al.

(10) Patent No.: US 11,839,561 B2
(45) Date of Patent: Dec. 12, 2023

(54) HANDLE FOR TWO-STAGE DEPLOYMENT OF A STENT

(71) Applicant: INSPIREMD Ltd., Tel Aviv (IL)

(72) Inventors: Juan Rigla, Manresa (ES); Shmuel Vered, Haifa (IL); Itshak Cohen, Ramat Hasharon (IL); Ryan Vincent Tien Sing Young, Dresden (DE); Alexandre Ioan Romoscanu, Geneva (CH)

(73) Assignee: INSPIRE M.D LTD., Tel Aviv (IL)

( * ) Notice: Subject to any disclaimer, the term of this patent is extended or adjusted under 35 U.S.C. 154(b) by 338 days.

(21) Appl. No.: 17/153,910

(22) Filed: Jan. 21, 2021

(65) Prior Publication Data

US 2022/0226135 A1    Jul. 21, 2022

(51) Int. Cl.
*A61F 2/95* (2013.01)
*A61F 2/966* (2013.01)
(Continued)

(52) U.S. Cl.
CPC ............ *A61F 2/9517* (2020.05); *A61F 2/966* (2013.01); *A61M 5/1452* (2013.01); *A61M 25/0097* (2013.01)

(58) Field of Classification Search
CPC .......... A61F 2/9517; A61F 2/95; A61F 2/966; A61F 2/2436; A61F 2/962; A61F 2210/0004; A61F 2002/9534; A61F 2/2427; A61F 2250/001; A61F 2250/0039; A61F 2250/0067; A61F 2210/0014; A61F 2/011;
(Continued)

(56) References Cited

U.S. PATENT DOCUMENTS

| | | | |
|---|---|---|---|
| 5,591,196 A | 1/1997 | Marin et al. | |
| 6,258,101 B1 * | 7/2001 | Blake, III | A61B 17/221 |
| | | | 606/113 |

(Continued)

FOREIGN PATENT DOCUMENTS

| | | |
|---|---|---|
| WO | 1999004728 A1 | 2/1999 |
| WO | 2014102890 A1 | 7/2014 |

(Continued)

OTHER PUBLICATIONS

Meaning of lever in English, (Apr. 5, 2023), Cambridge English Dictionary, pp. 1-11 (Year: 2023).*

(Continued)

*Primary Examiner* — Brooke Labranche
*Assistant Examiner* — Nasheha Baset
(74) *Attorney, Agent, or Firm* — KLIGLER & ASSOCIATES PATENT ATTORNEYS LTD

(57) ABSTRACT

An apparatus for retracting a sheath from over an expandable medical device includes a shell, configured to couple to a longitudinal element, a carriage disposed within the shell and configured to couple to the sheath, and a lever protruding from the shell. The lever is configured to retract the sheath while a distal end of the longitudinal element contacts the expandable medical device, by rotating proximally so as to move the carriage proximally by a first distance, and, subsequently to rotating proximally, sliding proximally so as to move the carriage proximally by a second distance. Other embodiments are also described.

21 Claims, 5 Drawing Sheets

(51) Int. Cl.
*A61M 5/145* (2006.01)
*A61M 25/00* (2006.01)

(58) Field of Classification Search
CPC ............ A61F 2/2466; A61M 25/0136; A61M 2205/103; A61M 25/0113; A61M 29/02; A61M 5/1452; A61M 25/0097; A61B 17/12022; A61B 17/1214; A61B 2017/00407; A61B 2017/12054; A61B 17/12113; A61B 2017/1205
See application file for complete search history.

(56) References Cited

U.S. PATENT DOCUMENTS

| | | | |
|---|---|---|---|
| 6,866,669 B2 | 3/2005 | Buzzard et al. | |
| 6,939,352 B2 | 9/2005 | Buzzard et al. | |
| 7,780,717 B2 | 8/2010 | Ducke et al. | |
| 7,935,141 B2 | 5/2011 | Randall et al. | |
| 7,976,574 B2 | 7/2011 | Papp | |
| 8,382,813 B2 | 2/2013 | Shumer | |
| 8,808,349 B2 | 8/2014 | Chuter et al. | |
| 8,814,931 B2 | 8/2014 | Wang et al. | |
| 9,039,750 B2 | 5/2015 | Ryan | |
| 9,198,788 B2 | 12/2015 | Murray, III et al. | |
| 9,486,350 B2 | 11/2016 | Argentine | |
| 9,867,701 B2 | 1/2018 | Morris et al. | |
| 10,258,491 B2 | 4/2019 | Bar et al. | |
| 10,327,927 B2 | 6/2019 | Ryan et al. | |
| 2001/0027323 A1 | 10/2001 | Sullivan, III et al. | |
| 2007/0191865 A1 | 8/2007 | Pappas | |
| 2009/0138023 A1 | 5/2009 | Johnson et al. | |
| 2010/0137967 A1* | 6/2010 | Atlani | A61F 2/95 623/1.11 |
| 2012/0123528 A1* | 5/2012 | Knippel | A61F 2/2436 623/2.11 |
| 2019/0247211 A1 | 8/2019 | Gilmartin et al. | |

FOREIGN PATENT DOCUMENTS

| | | | | |
|---|---|---|---|---|
| WO | WO-2016025896 A1 * | 2/2016 | ............ | A61F 2/82 |
| WO | 2016123503 A1 | 8/2016 | | |
| WO | WO-2016123503 A1 * | 8/2016 | ............ | A61F 2/95 |
| WO | WO-2020134593 A1 * | 7/2020 | ........... | A61F 2/9517 |

OTHER PUBLICATIONS

EP Application # 21211455.7 Search Report dated Jun. 15, 2022.
Cordis S.M.A.R.T. Control, product brochure, Cardinal Health, pp. 1-3, year 2017.

* cited by examiner

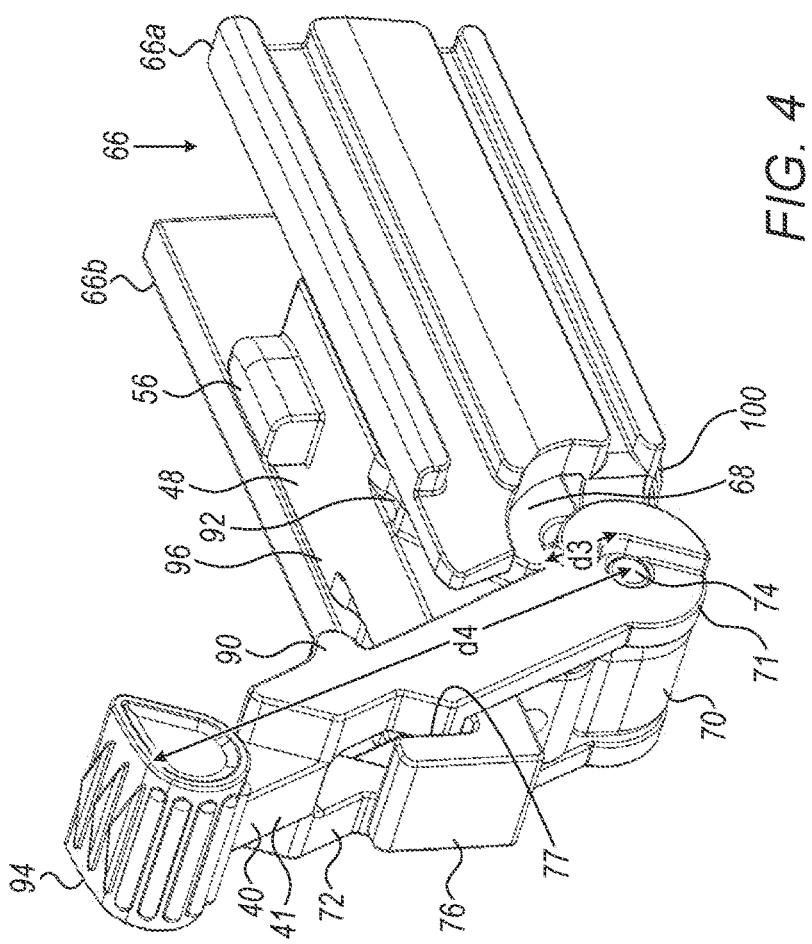
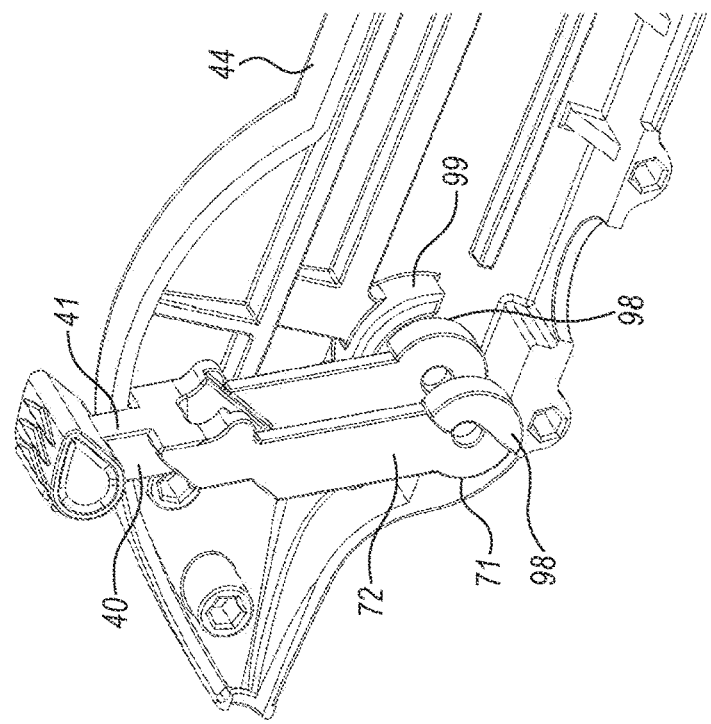
FIG. 4
FIG. 5

HANDLE FOR TWO-STAGE DEPLOYMENT OF A STENT

FIELD OF THE INVENTION

The present invention relates to the deployment of stents and other expandable devices within a body of a subject.

BACKGROUND

U.S. Pat. No. 9,867,701 describes a delivery device for a collapsible prosthetic heart valve, including an operating handle and a catheter assembly. The operating handle may include a housing defining a movement space therein, a carriage assembly moveable in a longitudinal direction within the movement space, a deployment actuator coupled to the housing and rotatable relative to the housing, and a coupling assembly rotationally fixed to the deployment actuator. The catheter assembly may include a first shaft around which a compartment is defined and a distal sheath operatively connected to the carriage assembly. Movement of the carriage assembly in the longitudinal direction in the movement space may move the distal sheath between the closed condition and the open condition. The coupling assembly may have an engaged position in which rotation of the deployment actuator moves the carriage assembly, and a disengaged position in which rotation of the deployment actuator does not move the carriage assembly.

U.S. Pat. No. 9,198,788 describes a delivery system to deliver and deploy a prosthesis in a body lumen, and methods of use thereof. The delivery system allows for operation of the delivery system with one hand while maintaining accuracy in delivery and deployment of the prosthesis. An exemplary embodiment of the delivery system includes a first sheath control on a housing so as to be accessible from the exterior of the housing, wherein the first sheath control is operatively engaged with the sheath and controls movement of the sheath axially proximally with respect to the housing, thereby releasing at least a portion of the prosthesis.

U.S. Pat. No. 5,591,196 describes a method for intraluminal delivery and deployment of an expandable prosthesis at a site within a body lumen. The method comprises the steps of placing the prosthesis over a support having at least two movable wings mounted on a catheter, delivering the prosthesis to the desired location by moving the catheter through the body passageway, and moving the wings radially outwardly to thereby deploy the prosthesis within the body passageway.

U.S. Pat. No. 7,976,574 describes a delivery system utilizing a handle assembly including an actuating mechanism capable of initially providing sufficient mechanical advantage to overcome static friction when initiating deployment of the medical device. The actuating mechanism includes components which help to increase the speed of deployment as the physician continues to manipulate the actuating mechanism.

U.S. Pat. No. 10,327,927 describes a vascular intervention device delivery system including a catheter with a proximal end attached to a handle, and a distal carrier segment for mounting a vascular intervention device thereon. A retractable sheath is movable from a first position covering the distal carrier segment to a second position retracted proximally uncovering the distal carrier segment. A pull is attached to the retractable sheath and extends proximally from the retractable sheath toward the handle. A majority of the length of the pull has a cross sectional shape with a concave side that faces the longitudinal axis and is opposite to a convex side that faces away from the longitudinal axis. The cross sectional shape has a width that is greater than a thickness.

US Patent Application Publication 2009/0138023 describes an actuator handle for use with an implantable medical device deployment system. The actuator handle includes a first actuator and a second actuator for manipulating and controlling first and second retaining members of the deployment system to effectuate release of a medical device from the deployment system.

SUMMARY OF THE INVENTION

There is provided, in accordance with some embodiments of the present invention, an apparatus for retracting a sheath from over an expandable medical device. The apparatus includes a shell, configured to couple to a longitudinal element, a carriage disposed within the shell and configured to couple to the sheath, and a lever protruding from the shell and configured to retract the sheath while a distal end of the longitudinal element contacts the expandable medical device, by rotating proximally so as to move the carriage proximally by a first distance, and, subsequently to rotating proximally, sliding proximally so as to move the carriage proximally by a second distance.

In some embodiments, the carriage is configured to couple to the sheath via one or more other longitudinal elements.

In some embodiments,
the carriage is shaped to define:
    a port configured to receive a distal end of a syringe, and
    a lumen in fluid communication with the port, and
the carriage is configured to couple to the sheath by gripping the sheath, or another longitudinal element coupled to the sheath, within the lumen, such that fluid injected from the syringe flows through the sheath via the lumen.

In some embodiments,
the shell is shaped to define a slit, and
the lever is configured to rotate proximally, and to slide proximally, within the slit.

In some embodiments,
the shell includes a distal arcuate portion and a proximal straight portion,
the lever is configured to rotate proximally while protruding from the distal arcuate portion, and
the lever is configured to slide proximally while protruding from the proximal straight portion.

In some embodiments, the first distance is between 5 and 10 mm.

In some embodiments,
the carriage is an inner carriage,
the apparatus further includes an outer carriage, and
the lever is rotatably coupled to the outer carriage such that the lever is configured to move the inner carriage proximally with respect to the outer carriage by the first distance, and to move the inner carriage, together with the outer carriage, proximally by the second distance.

In some embodiments, the apparatus further includes a stopper within the shell,
the shell is configured to couple to the longitudinal element by virtue of the stopper being coupled to an inside of the shell and to a proximal end of the longitudinal element, and the lever is configured to move the carriage proximally until movement of the carriage is stopped by the stopper.

In some embodiments, an axial position of the stopper is adjustable.

In some embodiments, a base of the lever is shaped to define at least one outwardly-protruding protrusion, and an inner wall of the shell is shaped to define at least one inwardly-protruding protrusion aligned with the outwardly-protruding protrusion while the lever is rotating proximally such that, while the lever is rotating proximally, the inwardly-protruding protrusion inhibits the base of the lever from sliding proximally.

In some embodiments,
the lever is shaped to define at least one protrusion, and
the carriage is shaped to define at least one depression configured to receive the protrusion following the rotation of the lever.

In some embodiments,
the carriage is shaped to define a distal L-shaped protrusion, and
the lever includes two legs that straddle the distal L-shaped protrusion such that, prior to the rotation of the lever, a vertical proximally-facing face of the distal L-shaped protrusion contacts the lever.

There is further provided, in accordance with some embodiments of the present invention, a method for retracting a sheath from over an expandable medical device. The method includes rotating a lever, which protrudes from a shell of a handle, proximally, such that the lever proximally moves, by a first distance, a carriage disposed within the shell and coupled to the sheath. The method further includes, subsequently to rotating the lever, sliding the lever proximally such that the lever moves the carriage proximally by a second distance.

In some embodiments,
the carriage is shaped to define a port and a lumen in fluid communication with the port,
the carriage is configured to couple to the sheath by gripping the sheath, or another longitudinal element coupled to the sheath, within the lumen, and
the method further includes, prior to rotating the lever, flushing the sheath by:
inserting a distal end of a syringe into the port, and
injecting fluid from the syringe into the port or the lumen such that the fluid flows through the sheath via the lumen.

There is further provided, in accordance with some embodiments of the present invention, a method including coupling a sheath to a carriage disposed within a shell of a handle, placing an expandable medical device within the sheath, and coupling a proximal end of a longitudinal element to a stopper disposed within the shell proximally to the carriage. The method further includes, subsequently to placing the expandable medical device within the sheath and coupling the proximal end of the longitudinal element to the stopper, moving the stopper distally until a distal end of the longitudinal element contacts the expandable medical device, and, subsequently to moving the stopper distally, fixing the stopper in place.

In some embodiments, an inner wall of the shell is shaped to define one or more tracks, and moving the stopper distally includes sliding the stopper distally along the tracks.

In some embodiments, a proximal end of the shell is shaped to define an opening, and moving the stopper distally includes pushing the stopper distally using a pushing element inserted through the opening.

In some embodiments, fixing the stopper in place includes fixing the stopper in place by screwing the stopper to the shell.

The present invention will be more fully understood from the following detailed description of embodiments thereof, taken together with the drawings, in which:

BRIEF DESCRIPTION OF THE DRAWINGS

FIG. 4 is a schematic illustration of a portion of a handle, including a carriage and a lever, in accordance with some embodiments of the present invention;

FIG. 5 is a schematic illustration of a lever and a shell, in accordance with some embodiments of the present invention.

DETAILED DESCRIPTION OF EMBODIMENTS

Overview

Typically, to deploy an expandable medical device such as a stent, a sheath is retracted from over the device, thus exposing the device such that the device expands. However, the amount of static friction between the sheath and the device may be relatively large, particularly if the device was compressed within the sheath for an extended period of time. As a result, it may be difficult to retract the sheath in a controlled and steady manner.

To address this challenge, embodiments of the present invention provide a handle configured to deploy an expandable medical device in a two-stage process. The handle comprises a lever and a carriage, which is coupled directly or indirectly to the sheath. In the first stage of deployment, the lever is rotated so as to move the carriage proximally by a first, relatively small distance. Subsequently, in the second stage of deployment, the lever is slid proximally, thus moving the carriage proximally by a second, larger distance.

Advantageously, the mechanical advantage provided by the lever during the first deployment stage facilitates overcoming the friction force between the sheath and the device. Moreover, due to the limited movement of the carriage during the first deployment stage, the first deployment stage does not expose the device; rather, the device is exposed, in a controlled and steady manner, only during the second stage of deployment.

System Description

Figure 1:
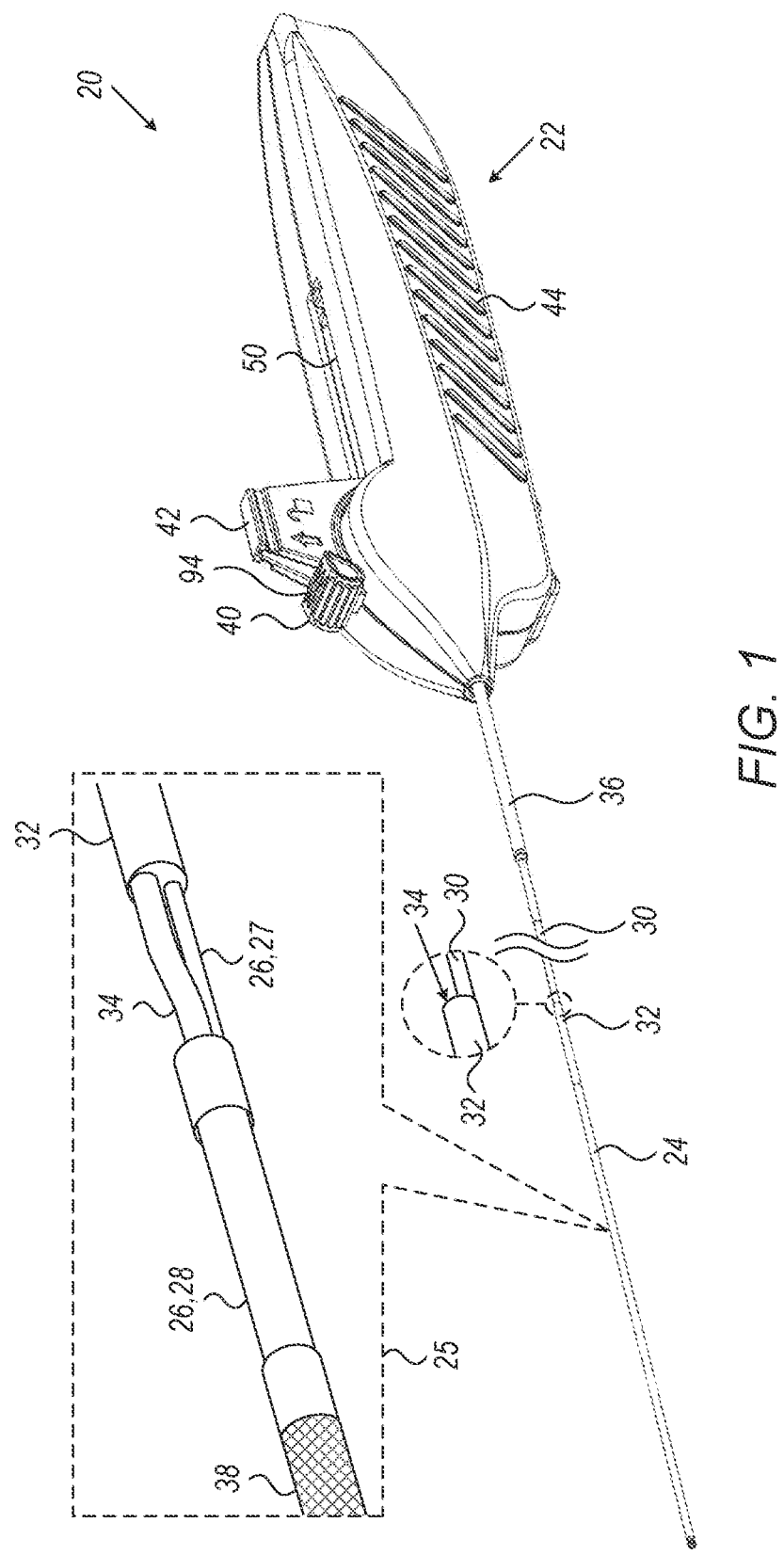
FIG. 1 is a schematic illustration of a system for treatment of a subject, in accordance with some embodiments of the present invention.

Reference is initially made to FIG. 1, which is a schematic illustration of a system 20 for treatment of a subject, in accordance with some embodiments of the present invention.

System 20 comprises a sheath 24. As shown in the inset portion 25 of FIG. 1, which shows the contents of sheath 24, the sheath is configured to contain an expandable medical device 38 in a crimped (unexpanded) configuration. Device 38 may comprise, for example, a stent (e.g., a mesh stent or a covered stent), a flow diverter, an aneurysm graft, or a heart valve.

System 20 further comprises a handle 22 for deploying device 38 from sheath 24 within a body cavity, such as a blood vessel, of the subject. Handle 22 comprises a shell 44, which may be made from a plastic or any other suitable material, and a lever 40, which protrudes from shell 44. When using the handle, a user, such as a physician, typically grips shell 44 with one hand, with the thumb of the hand placed over the head 94 of the lever. (Optionally, head 94 may be shaped to define bumps, which inhibit the thumb from slipping off the head.) Alternatively, the user may grasp head 94 with his other hand.

Figure 2:
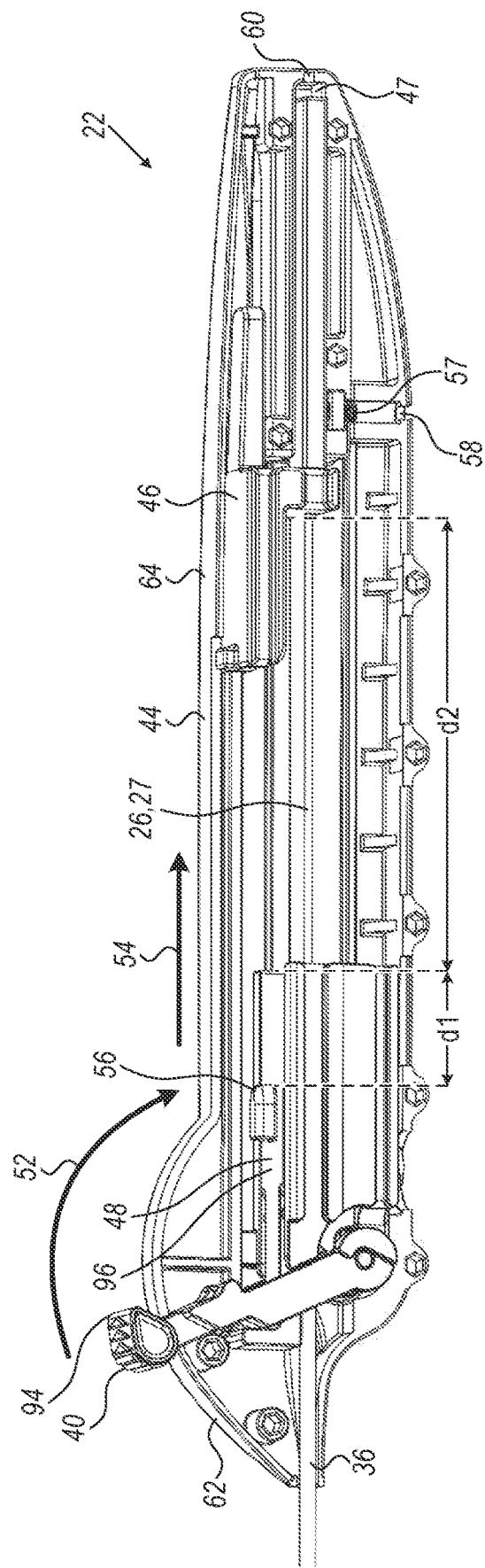
FIGS. 2-3 are schematic illustrations of a handle, in accordance with some embodiments of the present invention.

Reference is now additionally made to FIG. 2, which is a schematic illustration of handle 22, in accordance with some embodiments of the present invention. A portion of shell 44 is hidden from view in FIG. 2, so as to expose components of the handle contained within the shell.

Handle 22 comprises a carriage 48 disposed within shell 44 and configured to couple to sheath 24. As further described below, by manipulating lever 40, the user moves the carriage proximally, thus retracting sheath 24 from over device 38 such that the device expands within the body cavity.

Figure 6:
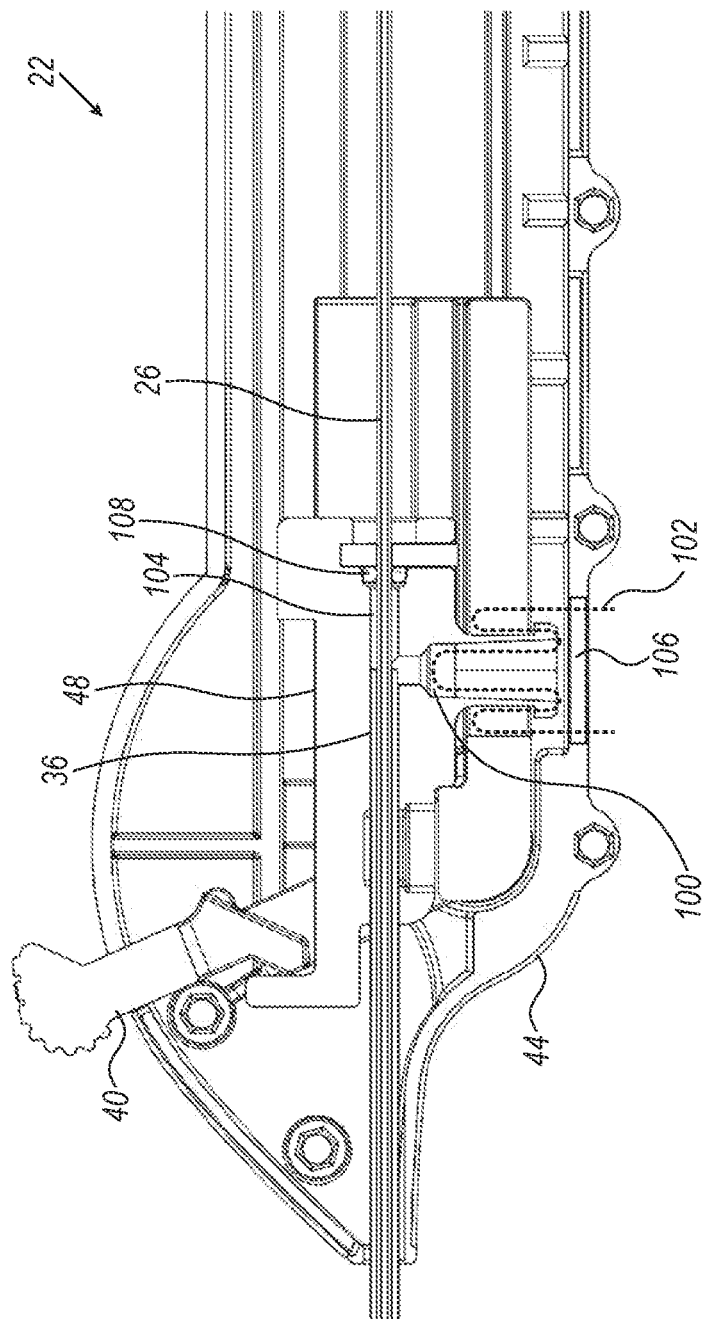
FIG. 6 is a schematic illustration of a longitudinal cross-section through a distal portion of a handle, in accordance with some embodiments of the present invention.

Typically, the carriage is not coupled directly to the sheath, but rather, is coupled to the sheath via one or more longitudinal elements. For example, the inner wall of the sheath may be coupled to a rapid exchange tube 32, which in turn may be coupled to a flexible tube 30. Flexible tube 30, in turn, may be coupled to a reinforced tube 36, which is coupled to the carriage. For example, as shown in FIG. 6 (described below), reinforced tube 36 may be gripped within a lumen of the carriage, e.g., by virtue of being glued to the wall of the lumen. Typically, flexible tube 30 has a length between 20 cm and 1.5 m, so as to extend from the exterior of the subject to the site at which the expandable device is to be deployed.

Shell 44 is configured to couple to a longitudinal element 26. As the lever retracts the sheath by moving the carriage proximally relative to shell 44, the distal end of longitudinal element 26 remains in contact with the expandable medical device. Thus, longitudinal element 26 inhibits retraction of the expandable medical device (i.e., the longitudinal element provides a distal counterforce to the device), such that the sheath is retracted from over the expandable medical device.

Typically, longitudinal element 26 comprises a flexible wire 27, which is distally coupled to a distal tube 28. Typically, flexible wire 27 has a length between 20 cm and 1.5 m.

Prior to deploying the expandable medical device, the sheath (together with the expandable device disposed therein) is navigated, typically under fluoroscopy, to the site at which the device is to be deployed. In some embodiments, the sheath is navigated over a guidewire. The guidewire may be passed through a guidewire tube 34, which runs through rapid exchange tube 32 and distal tube 28.

Typically, shell 44 is shaped to define a slit 50, and lever 40 is configured to move proximally within slit 50. In some embodiments, system 20 further comprises a safety tab 42, which fits into the slit proximally to lever 40 so as to lock the lever in place, i.e., inhibit any unintended movement of the lever. Prior to deploying the expandable medical device, tab 42 is removed from the handle.

Deploying the Expandable Medical Device

Advantageously, as described above in the Overview, handle 22 facilitates a two-stage deployment of device 38.

During the first stage, lever 40 is rotated proximally, as indicated in FIG. 2 by a rotation indicator 52. (In the context of the present application, including the claims, a "proximal rotation" of the lever refers to a rotation of the lever in which head 94 of the lever moves proximally.) The rotation of the lever moves the carriage proximally by a first distance d1, which in some embodiments is between 5 and 10 mm. Advantageously, the mechanical advantage provided by the lever facilitates overcoming the friction between the sheath and the expandable device.

Typically, during the first stage of deployment, the lever is rotated until the lever contacts the top face 96 of carriage 48, such that the carriage inhibits further rotation of the lever.

During the second stage, the lever is slid proximally, as indicated in FIG. 2 by a sliding indicator 54. The sliding of the lever moves the carriage proximally by a second distance d2.

Typically, shell 44 is coupled to longitudinal element 26 via a stopper 46, in that stopper 46 is coupled to the inside of the shell (e.g., via a screw 57, as described below) and to the proximal end of longitudinal element 26 (e.g., via glue inserted through the shell). (Stopper 46 may comprise a piece of material, such as a piece of plastic, having any suitable shape.) During the second stage of deployment, carriage 48 is moved proximally until the movement of the carriage is stopped by stopper 46, e.g., by virtue of a protrusion 56, which protrudes upwardly from the carriage, fitting into a complementary depression in the underside of the stopper.

Typically, the axial position of stopper 46—i.e., the position of the stopper along an axis running between the proximal and distal ends of the handle—is adjustable. For example, the inner wall of the shell may be shaped to define one or more tracks 47, and the stopper may be configured to slide along tracks 47. During the assembly of system 20, the sheath is coupled to the carriage, the expandable medical device is placed within the sheath, and the proximal end of the longitudinal element is coupled to the stopper. (The latter three steps may be performed in any suitable order.) Stopper 46 is then moved distally until the distal end of longitudinal element 26 contacts the expandable device. For example, the proximal end of the shell may be shaped to define an opening 60, and the stopper may be pushed distally by a pushing element (e.g., a finger or a tool) inserted through opening 60. Subsequently, the stopper is fixed in place, e.g., by inserting screw 57 through a screw-hole 58 in shell 44 and, using the screw, screwing the stopper to the shell.

In general, the expandable device is placed within the sheath such that the distance separating the distal end of the device from the distal end of the sheath is greater than d1 but less than $d2_{min}$-L, $d2_{min}$ being the minimum expected value of d2 following the adjustment of the stopper, and L being the length of the expandable device (e.g., 20, 30, 40, or 60 mm). By virtue of the distance being greater than d1, the device does not exit the sheath (even partly) during the first stage of deployment, even in a case of minimal friction between the sheath and the device, in which case the sheath is retracted by d1. By virtue of the distance being less than $d2_{min}$-L, the device exits the sheath during the second stage of deployment even in a case of maximal friction between the sheath and the device, in which case the sheath is not retracted at all during the first stage.

Typically, the shell comprises a distal arcuate portion 62 and a proximal straight portion 64. The lever is configured to rotate proximally while protruding from distal arcuate portion 62, typically with head 94 being situated a small distance (e.g., 1-5 mm) from the distal arcuate portion. The lever is further configured to slide proximally while protruding from proximal straight portion 64, typically with head 94 being situated a small distance (e.g., 1-5 mm) from the proximal straight portion.

Advantageously, distal arcuate portion 62 helps the user ascertain the moment at which the first deployment stage ends and the second stage begins. Furthermore, the distal arcuate portion may facilitate locking the lever prior to deployment, e.g., using safety tab 42.

Figure 3:
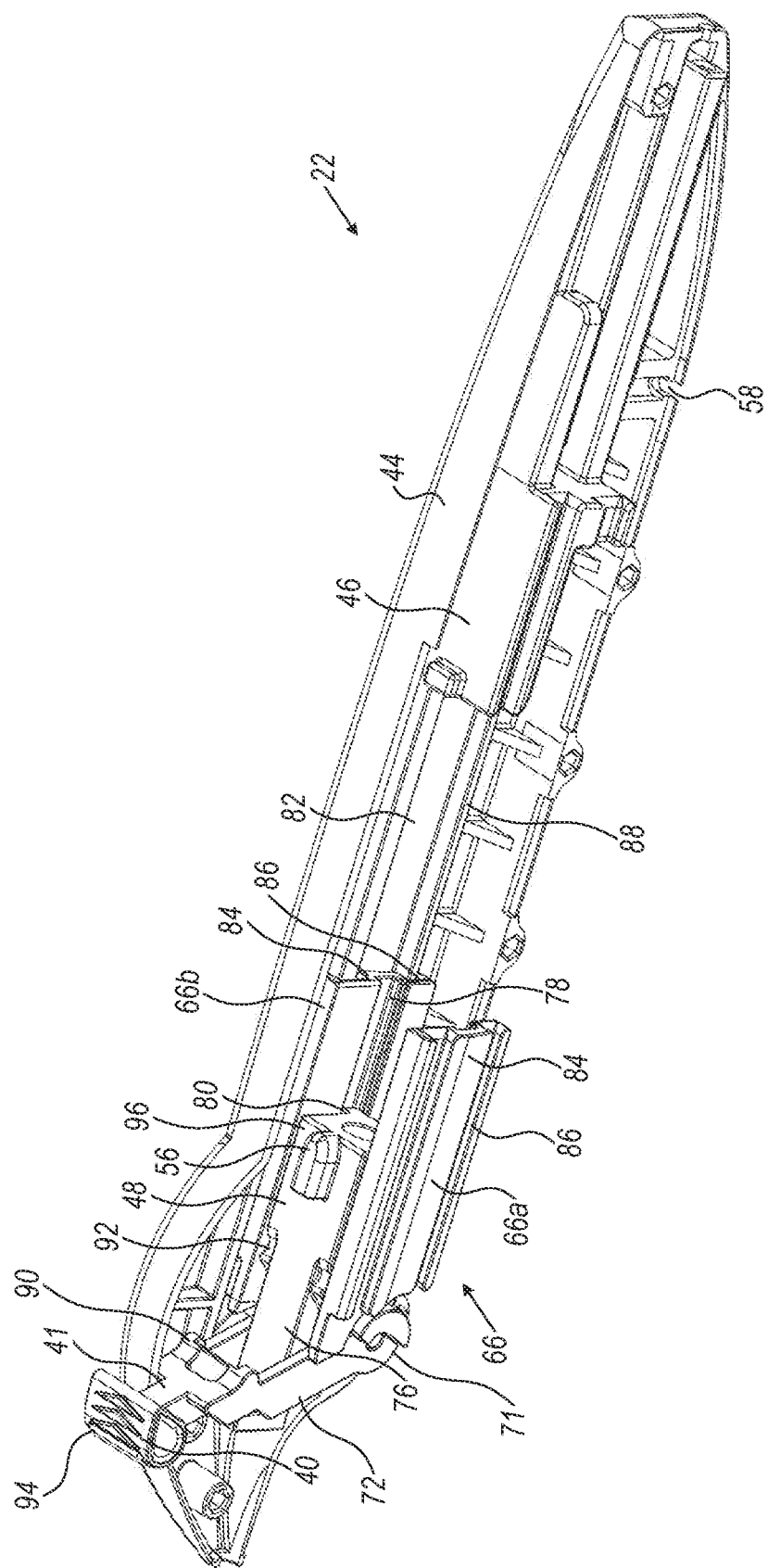

Reference is now made to FIG. 3, which is another schematic illustration of handle 22, in accordance with some embodiments of the present invention. (As in FIG. 2, a portion of shell 44 is hidden from view so as to expose the interior of the handle.) Reference is also made to FIG. 4, which is a schematic illustration of a portion of handle 22, including carriage 48 and lever 40, in accordance with some embodiments of the present invention.

Typically, the lever comprises a neck 41, which extends along the longitudinal axis of the lever, along with two legs 72, which extend along the longitudinal axis of the lever between neck 41 and the base 71 of the lever. (Neck 41 thus joins legs 72 to head 94.) Typically, legs 72 are disposed at opposite sides of neck 41, such that neck 41 is aligned with slit 50 (FIG. 1) while legs 72 are disposed beneath the shell at opposing sides of the slit. Thus, during the second stage of deployment, the shell inhibits the lever from rotating distally.

In some embodiments, legs 72 straddle a distal L-shaped protrusion 16 of carriage 48. Prior to the rotation of the lever, the vertical proximally-facing face 17 of protrusion 76 contacts the lever, such that the lever inhibits carriage 48 from sliding proximally.

In some embodiments, the lever is shaped to define at least one protrusion 90, such as a respective protrusion 90 on each leg 72 of the lever. Additionally, the carriage (in particular, top face 96) is shaped to define at least one depression 92 configured to receive protrusion 90 following the rotation of the lever. For example, the carriage may be shaped to define two depressions 92, each depression 92 aligned with a respective leg 72 such that the depression is configured to receive the protrusion on the leg. By virtue of the protrusions fitting into the depressions, the carriage does not slide proximally away from the lever during the second stage of deployment.

Typically, carriage 48 is shaped to define one or more distal protrusions 68 that contact lever 40; for example, the carriage may be shaped to define two protrusions 68, each of which contacts a different respective leg 72 of the lever. As the lever is rotated, the lever pushes against protrusions 68, thus moving the carriage proximally. Distance d1—the distance by which carriage 48 is moved during the first stage of deployment—may be adjusted by varying the distance d3 between the axis of rotation of the lever and protrusions 68; as d3 is increased, d1 increases. (It is noted that the mechanical advantage d4/d3 of the lever, where d4 is the distance from the axis of rotation to the top of the head of the lever, also varies with d3.)

Alternatively or additionally to protrusions 68, the carriage may be shaped to define one or more distally-protruding racks, and the base 71 of the lever—comprising, for example, the respective bases of legs 12—may be shaped to define one or more partial pinions that contact the racks. As the lever rotates, the pinions may move the racks proximally, thus moving the carriage.

It is noted that, in addition to the distance between the axis of rotation and the point of contact between the lever and the carriage, distance d1 is a function of the angle by which the lever is rotated. In some embodiments, this angle is between 25 and 90 degrees.

Typically, handle 22 further comprises an outer carriage 66. In such embodiments, lever 40 is rotatably coupled to outer carriage 66 such that the lever is configured to move carriage 48—which may be referred to, in such embodiments, as an "inner carriage"—proximally with respect to the outer carriage by distance d1 (FIG. 2) during the first stage of deployment. Subsequently, during the second stage of deployment, the lever moves the inner carriage, together with the outer carriage, proximally by distance d2.

In some embodiments, as shown in FIGS. 3-4, outer carriage 66 comprises a first carriage wall 66a and a second carriage wall 66b joined to one another by a distal carriage bottom 70. Alternatively, the outer carriage may comprise a single carriage wall joined to carriage bottom 70. In either case, lever 40 is typically coupled to carriage bottom 70. For example, the carriage bottom may comprise respective pins 74 on opposite sides of the carriage bottom (or a single pin passing through the carriage bottom), and the respective bases of legs 72 may be fitted over pins 74 such that the pins define the axis of rotation of the lever.

In some embodiments, as shown in FIG. 3, outer carriage 66 is shaped to define at least one groove 78, and inner carriage 48 is shaped to define at least one protrusion 80 configured to slide within groove 78 while, during the first stage of deployment, the lever moves the inner carriage proximally with respect to the outer carriage. For example, each of first carriage wall 66a and second carriage wall 66b may be shaped to define a respective groove 78, and the inner carriage may be shaped to define two protrusions 80 on opposite sides of the inner carriage such that each of the protrusions slides within a different respective groove 78. Alternatively or additionally, the inner carriage may be shaped to define at least one groove, and the outer carriage may be shaped to define at least one protrusion configured to slide within the groove during the first stage of deployment. Advantageously, the aforementioned grooves and protrusions guide the movement of the inner carriage within the outer carriage.

Similarly, shell 44 may be shaped to define at least one groove 82, and outer carriage 66 may be shaped to define at least one protrusion 84 configured to slide within groove 82 while, during the second stage of deployment, the lever moves the inner and outer carriages proximally with respect to the shell. Alternatively or additionally, the outer carriage may be shaped to define at least one groove 86, and the shell may be shaped to define at least one protrusion 88 configured to slide within groove 86 during the second stage of deployment. For example, each of first carriage wall 66a and second carriage wall 66b may be shaped to define a respective protrusion 84, along with a pair of grooves 86 on opposite sides of the protrusion. Complementarily, each wall of the shell may be shaped to define a groove 82, within which a protrusion 84 of one of the carriage walls slides, along with a pair of protrusions 88 on opposite sides of the groove, which slide within grooves 86 of the wall. Advantageously, the aforementioned grooves and protrusions guide the movement of the outer carriage within the shell.

In alternate embodiments, the handle does not comprise an outer carriage. Rather, carriage 48 comprises a proximal portion, a distal portion, and a compressible middle portion (comprising a spring, for example) that joins the proximal portion to the distal portion. During the rotation of the lever, the distal portion of the carriage is moved toward the proximal portion of the carriage as the middle portion is compressed. Subsequently, the entire carriage is moved proximally by the sliding of the lever.

Reference is now made to FIG. 5, which is a schematic illustration of lever 40 and shell 44, in accordance with some embodiments of the present invention. (Other components of the handle, such as the carriages, are omitted from FIG. 5.)

In some embodiments, base 71 is shaped to define at least one outwardly-protruding arcuate protrusion 98, and the inner wall of the shell is shaped to define at least one inwardly-protruding arcuate protrusion 99. During the first deployment stage, protrusion 99 is aligned with protrusion 98 such that, while the lever is rotating, protrusion 99 inhibits the base of the lever from sliding proximally. For example, the base of each leg 72 may be shaped to define a respective protrusion 98, each of which is aligned with a different respective protrusion 99 during the first deployment stage. As the lever completes its rotation, protrusion 98 drops below protrusion 99, such that the base of the lever is free to slide proximally during the second deployment stage.

Flushing the Sheath

Reference is now made to FIG. 6, which is a schematic illustration of a longitudinal cross-section through a distal portion of handle 22, in accordance with some embodiments of the present invention.

Typically, carriage 48 is shaped to define a port 100, such as a female Luer port, configured to receive (e.g., via an opening 106 in the shell) the distal end of a syringe 102. (It is noted that the bottom of port 100 is shown in FIG. 4.) Typically, carriage 48 is further shaped to define a lumen 104 in fluid communication with port 100.

In such embodiments, as described above with reference to FIGS. 1-2, the carriage is configured to couple to sheath 24 (FIG. 1) by gripping the sheath, or another longitudinal element (such as reinforced tube 36) coupled to the sheath, within lumen 104. Thus, prior to the deployment of the device, the sheath may be flushed with a fluid, such as saline, injected from syringe 102. In particular, the fluid may be injected into port 100 (and/or directly into lumen 104) such that the fluid flows through the sheath via the lumen. For example, the fluid may flow through the sheath via lumen 104, reinforced tube 36, flexible tube 30, and rapid exchange tube 32, which, as described above with reference to FIG. 1, is coupled to the inside of the sheath.

In some embodiments, as shown in FIG. 6, longitudinal element 26 passes through lumen 104. In such embodiments, a seal 108, such as an O-ring, may be placed around the longitudinal element within lumen 104 and proximally to port 100, so as to inhibit the flow of fluid through the proximal end of the lumen.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. Apparatus for retracting a sheath from over an expandable medical device, the apparatus comprising:
    a shell, configured to couple to a longitudinal element;
    an outer carriage disposed within the shell;
    an inner carriage disposed within the outer carriage and configured to couple to the sheath; and
    a lever protruding from the shell and rotatably coupled to the outer carriage, and configured to retract the sheath while a distal end of the longitudinal element contacts the expandable medical device, by:
        rotating proximally so as to move the inner carriage proximally, with respect to the outer carriage, by a first distance, and
        subsequently to rotating proximally, sliding proximally so as to move the inner carriage, together with the outer carriage, proximally by a second distance.

2. The apparatus according to claim 1, wherein the inner carriage is configured to couple to the sheath via one or more other longitudinal elements.

3. The apparatus according to claim 1,
    wherein the inner carriage is shaped to define:
        a port configured to receive a distal end of a syringe, and
        a lumen in fluid communication with the port, and
    wherein the inner carriage is configured to couple to the sheath by gripping the sheath, or another longitudinal element coupled to the sheath, within the lumen, such that fluid injected from the syringe flows through the sheath via the lumen.

4. The apparatus according to claim 1,
    wherein the shell is shaped to define a slit, and
    wherein the lever is configured to rotate proximally, and to slide proximally, within the slit.

5. The apparatus according to claim 1,
    wherein the shell comprises a distal arcuate portion and a proximal straight portion,
    wherein the lever is configured to rotate proximally while protruding from the distal arcuate portion, and
    wherein the lever is configured to slide proximally while protruding from the proximal straight portion.

6. The apparatus according to claim 1, wherein the first distance is between 5 and 10 mm.

7. The apparatus according to claim 1, further comprising a stopper coupled to an inside of the shell and
    configured to couple to a proximal end of the longitudinal element, thereby coupling the shell to the longitudinal element,
    wherein the lever is configured to move the inner carriage proximally until movement of the inner carriage is stopped by the stopper.

8. The apparatus according to claim 7, wherein an axial position of the stopper is adjustable.

9. The apparatus according to claim 1, wherein a base of the lever is shaped to define at least one outwardly-protruding protrusion, and wherein an inner wall of the shell is shaped to define at least one inwardly-protruding protrusion aligned with the outwardly-protruding protrusion while the lever is rotating proximally such that, while the lever is rotating proximally, the inwardly-protruding protrusion inhibits the base of the lever from sliding proximally.

10. The apparatus according to claim 1,
    wherein the lever is shaped to define at least one protrusion, and
    wherein the inner carriage is shaped to define at least one depression configured to receive the protrusion following the rotation of the lever.

11. The apparatus according to claim 1,
wherein the inner carriage is shaped to define a distal L-shaped protrusion, and
wherein the lever comprises two legs that straddle the distal L-shaped protrusion such that, prior to the rotation of the lever, a vertical proximally-facing face of the distal L-shaped protrusion contacts the lever.

12. Apparatus for retracting a sheath from over an expandable medical device, the apparatus comprising:
a shell, configured to couple to a longitudinal element;
a carriage disposed within the shell and configured to couple to the sheath; and
a lever protruding from the shell and configured to retract the sheath while a distal end of the longitudinal element contacts the expandable medical device, by:
rotating proximally so as to move the carriage proximally by a first distance, and
subsequently to rotating proximally, sliding proximally so as to move the carriage proximally by a second distance,
wherein a base of the lever is shaped to define at least one outwardly-protruding protrusion, and
wherein an inner wall of the shell is shaped to define at least one inwardly-protruding protrusion aligned with the outwardly-protruding protrusion while the lever is rotating proximally such that, while the lever is rotating proximally, the inwardly-protruding protrusion inhibits the base of the lever from sliding proximally.

13. Apparatus for retracting a sheath from over an expandable medical device, the apparatus comprising:
a shell, configured to couple to a longitudinal element;
a carriage disposed within the shell and configured to couple to the sheath; and
a lever protruding from the shell and configured to retract the sheath while a distal end of the longitudinal element contacts the expandable medical device, by:
rotating proximally so as to move the carriage proximally by a first distance, and
subsequently to rotating proximally, sliding proximally so as to move the carriage proximally by a second distance,
wherein the carriage is shaped to define a distal L-shaped protrusion, and
wherein the lever comprises two legs that straddle the distal L-shaped protrusion such that, prior to the rotation of the lever, a vertical proximally-facing face of the distal L-shaped protrusion contacts the lever.

14. The apparatus according to claim 13,
wherein the carriage is shaped to define:
a port configured to receive a distal end of a syringe, and
a lumen in fluid communication with the port, and
wherein the carriage is configured to couple to the sheath by gripping the sheath, or another longitudinal element coupled to the sheath, within the lumen, such that fluid injected from the syringe flows through the sheath via the lumen.

15. The apparatus according to claim 13, wherein the first distance is between 5 and 10 mm.

16. The apparatus according to claim 13,
wherein the lever is shaped to define at least one protrusion, and
wherein the carriage is shaped to define at least one depression configured to receive the protrusion following the rotation of the lever.

17. Apparatus for retracting a sheath from over an expandable medical device, the apparatus comprising:
a shell;
a stopper coupled to an inside of the shell and configured to couple to a proximal end of a longitudinal element;
a carriage disposed within the shell and configured to couple to the sheath; and
a lever protruding from the shell and configured to retract the sheath while a distal end of the longitudinal element contacts the expandable medical device, by:
rotating proximally so as to move the carriage proximally by a first distance, and
subsequently to rotating proximally, sliding proximally so as to move the carriage proximally, by a second distance, until movement of the carriage is stopped by the stopper.

18. The apparatus according to claim 17,
wherein the carriage is shaped to define:
a port configured to receive a distal end of a syringe, and
a lumen in fluid communication with the port, and
wherein the carriage is configured to couple to the sheath by gripping the sheath, or another longitudinal element coupled to the sheath, within the lumen, such that fluid injected from the syringe flows through the sheath via the lumen.

19. The apparatus according to claim 17, wherein the first distance is between 5 and 10 mm.

20. The apparatus according to claim 17, wherein an axial position of the stopper is adjustable.

21. The apparatus according to claim 17,
wherein the lever is shaped to define at least one protrusion, and
wherein the carriage is shaped to define at least one depression configured to receive the protrusion following the rotation of the lever.

* * * * *